(12) United States Patent
Piantoni et al.

(10) Patent No.: US 10,111,785 B2
(45) Date of Patent: Oct. 30, 2018

(54) MAKER MACHINE TO MANUFACTURE HYGIENE ABSORBENT ARTICLES

(71) Applicant: GDM S.p.A., Bologna (IT)

(72) Inventors: Matteo Piantoni, Albino (IT); Valerio Soli, Bologna (IT)

(73) Assignee: GDM S.p.A., Bologna (IT)

( * ) Notice: Subject to any disclaimer, the term of this patent is extended or adjusted under 35 U.S.C. 154(b) by 0 days.

(21) Appl. No.: 15/564,754

(22) PCT Filed: Apr. 8, 2016

(86) PCT No.: PCT/IB2016/052014
§ 371 (c)(1),
(2) Date: Oct. 6, 2017

(87) PCT Pub. No.: WO2016/162850
PCT Pub. Date: Oct. 13, 2016

(65) Prior Publication Data
US 2018/0104112 A1    Apr. 19, 2018

(30) Foreign Application Priority Data

Apr. 9, 2015   (IT) .............................. BO2015A0169

(51) Int. Cl.
*A61F 13/15* (2006.01)
*B65G 47/84* (2006.01)
*B65H 20/12* (2006.01)

(52) U.S. Cl.
CPC ...... *A61F 13/15764* (2013.01); *B65G 47/848* (2013.01); *B65H 20/12* (2013.01);
(Continued)

(58) Field of Classification Search
CPC .... B65G 47/84; B65G 47/848; B65G 47/846; B65G 47/847; B65G 47/484;
(Continued)

(56) References Cited

U.S. PATENT DOCUMENTS 6,692,196 B1 * 2/2004 Simm ............... A61F 13/15764
198/465.2
8,720,673 B2 * 5/2014 Loecht ................... B65G 19/02
198/619

(Continued)

FOREIGN PATENT DOCUMENTS

| EP | 2644174 A1 | 10/2013 | |
| WO | WO-2008/155618 A2 | 12/2008 | |
| WO | WO-2014167369 A1 * | 10/2014 | ........... B65G 47/848 |

OTHER PUBLICATIONS

International Preliminary Report on Patentability, International Application No. PCT/IB2016/052014, dated Mar. 8, 2017.

(Continued)

*Primary Examiner* — Mark A Deuble
(74) *Attorney, Agent, or Firm* — Marshall, Gerstein & Borun LLP

(57) ABSTRACT

Maker machine to manufacture hygiene absorbent articles and having: a feeding line which feeds a continuous strip of impermeable material, which is intended to define a succession of sheets of impermeable material; and at least one operating unit which feeds a corresponding component of the hygiene absorbent articles to the sheets of impermeable material carried by the feeding line by way of an application device; the application device has at least one sucking pick-up head and a conveyor provided with an annular guide which is arranged in fixed position along an application path, a slide which supports the sucking pick-up head and is coupled to the guide so as to freely slide along the guide, and a linear electric motor, which has a stator that is arranged in a fixed position along the guide and a mobile slider which is electro-magnetically coupled to the stator so as to receive, from the stator a driving force and is rigidly connected to the slide.

15 Claims, 19 Drawing Sheets

(52) U.S. Cl.
CPC ............... *A61F 2013/15845* (2013.01); *B65H 2404/154* (2013.01); *B65H 2406/33* (2013.01)

(58) Field of Classification Search
CPC ..... A61F 15/15764; A61F 2013/15845; B65H 20/12; B65H 2404/154; B65H 2406/33
See application file for complete search history.

(56) References Cited

U.S. PATENT DOCUMENTS

| | | | | |
|---|---|---|---|---|
| 8,827,071 | B2* | 9/2014 | van de Loecht | B65G 54/02 198/619 |
| 2004/0089516 | A1* | 5/2004 | Christian | A61F 13/15723 198/459.8 |
| 2010/0326796 | A1* | 12/2010 | Walsh | A61F 13/15764 198/579 |
| 2011/0088233 | A1 | 4/2011 | McCabe et al. | |
| 2013/0270069 | A1 | 10/2013 | Papsdorf et al. | |
| 2014/0353123 | A1* | 12/2014 | Schoultz | B65G 39/02 198/617 |
| 2015/0027338 | A1* | 1/2015 | Aumann | B65G 54/02 104/290 |
| 2015/0144462 | A1* | 5/2015 | Weiss | B65G 35/06 198/619 |
| 2016/0176659 | A1* | 6/2016 | Aumann | B65G 54/02 198/619 |

OTHER PUBLICATIONS

International Search Report and Written Opinion, International Application No. PCT/IB2016/052014, dated Jul. 14, 2016.

\* cited by examiner

MAKER MACHINE TO MANUFACTURE HYGIENE ABSORBENT ARTICLES

CROSS-REFERENCE TO RELATED APPLICATIONS

This is the U.S. national phase of International Application No. PCT/IB2016/052014, filed Apr. 8, 2015, which claims the benefit of Italian Patent Application No. BO2015A000169, filed Apr. 9, 2015.

TECHNICAL FIELD

The present invention relates to a maker machine to manufacture hygiene absorbent articles.

PRIOR ART

As known, hygiene absorbent articles comprise an impermeable layer (e.g. polyethylene), a non-woven fabric layer permeable to liquids, and an absorbent padding enclosed therebetween. Said components are the basic elements of an absorbent article. In addition to the basic components mentioned above, the absorbent articles further comprise accessory components (such as elastic bands, fecal barriers and lateral wings) which make the structure, as well as the manufacturing, more or less complex.

A known type maker machine for manufacturing hygiene absorbent articles (for example as described in patent application WO2008155618A1) comprises a feeding line of a continuous strip of impermeable material along which a plurality of operating units are arranged which feed the basic and accessory components intended to define the absorbent article, to the continuous strip.

Each operating unit comprises a processing device which receives in succession the respective components and processes the components themselves (e.g. a cut of the components) and an application device which receives the finished components from the processing device and applies the components to the continuous strip of impermeable material. Generally, the application device comprises a central drum which is hinged to rotate around a central rotation axis and a pair of radial support arms, each of which is hinged to the central drum to rotate, with respect to the central drum, around a rotation axis parallel to the rotation axis of the central drum and supports a sucking pick-up head adapted to receive, retain, and subsequently apply a corresponding component. Generally, also the sucking pick-up head can be hinged to the support arm to rotate with respect to the support arm around a rotation axis perpendicular to the rotation axis of the central drum. In known maker machines, in the application device the rotation of the radial arms with respect to the central drum and the possible rotation of the sucking pick-up heads with respect to the radial arms is mechanically controlled by means of a cam control system.

During a format change operation, i.e. during an operation that changes the maker machine to vary the type of hygiene absorbent articles which are made, it is often necessary to modify the law of motion of the sucking pick-up heads of the application device to adapt this law of motion to a different size and/or position of the components that are to be processed. Modifying the law of motion of the pick-up heads requires the replacement of some mechanical components (typically at least the corresponding cams) and said substitution is particularly long and complex because for the disassembly of the old mechanical components and for the subsequent assembly of the new mechanical components a setup step must follow, which is quite laborious and requires the intervention of a skilled technician.

DESCRIPTION OF THE INVENTION

The object of the present invention is to provide a maker machine to manufacture hygiene absorbent articles which is free from the drawbacks described above and, at the same time, is simple and inexpensive to manufacture.

According to the present invention, a maker machine to manufacture hygiene absorbent articles, as claimed in the attached claims is provided.

BRIEF DESCRIPTION OF THE DRAWINGS

The present invention will now be described with reference to the accompanying drawings, which illustrate some examples of non-limiting embodiments, wherein.

PREFERRED EMBODIMENTS OF THE INVENTION

Figure 1:
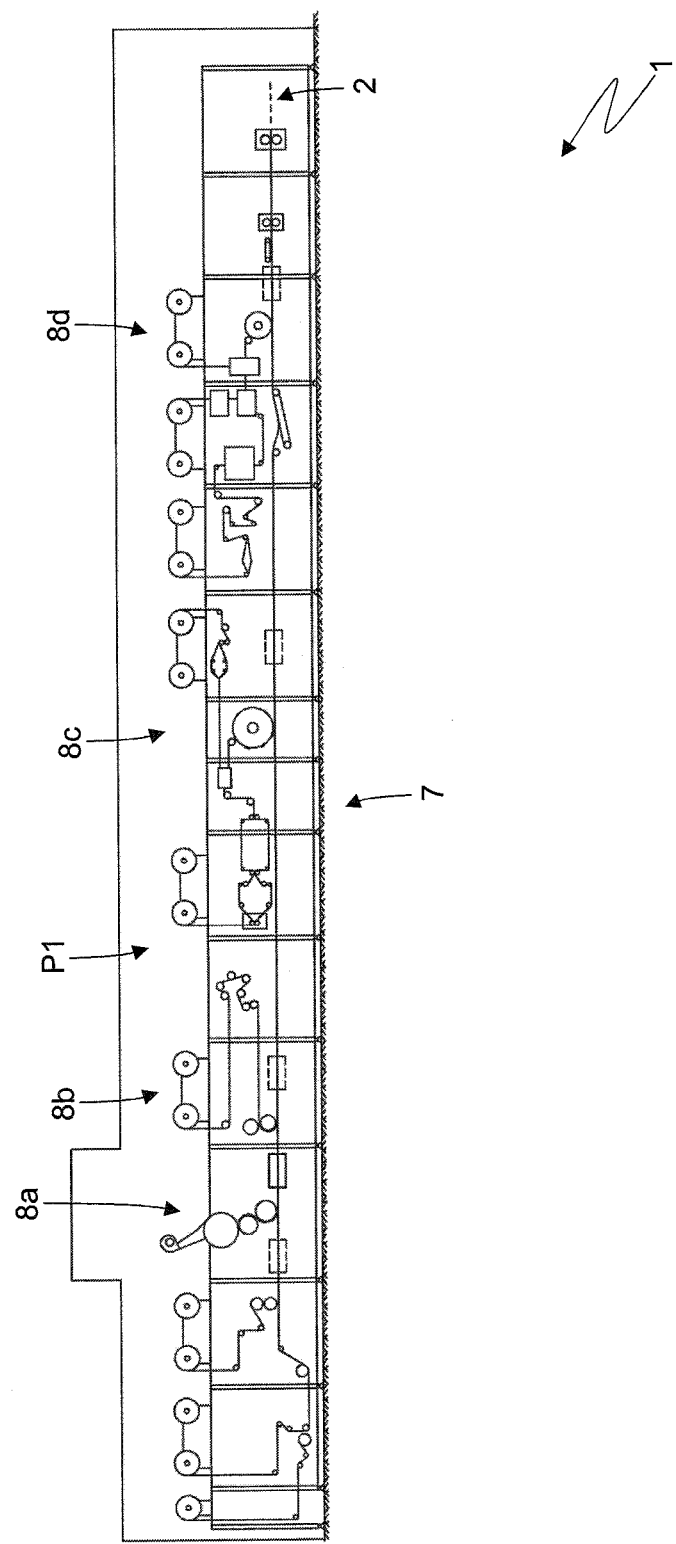
FIG. 1 is a schematic front view of a maker machine to manufacture hygiene absorbent articles manufactured according to the present invention.

In FIG. 1, number 1 denotes as a whole a maker machine to manufacture hygiene absorbent articles 2 (for example diapers).

Figure 2:
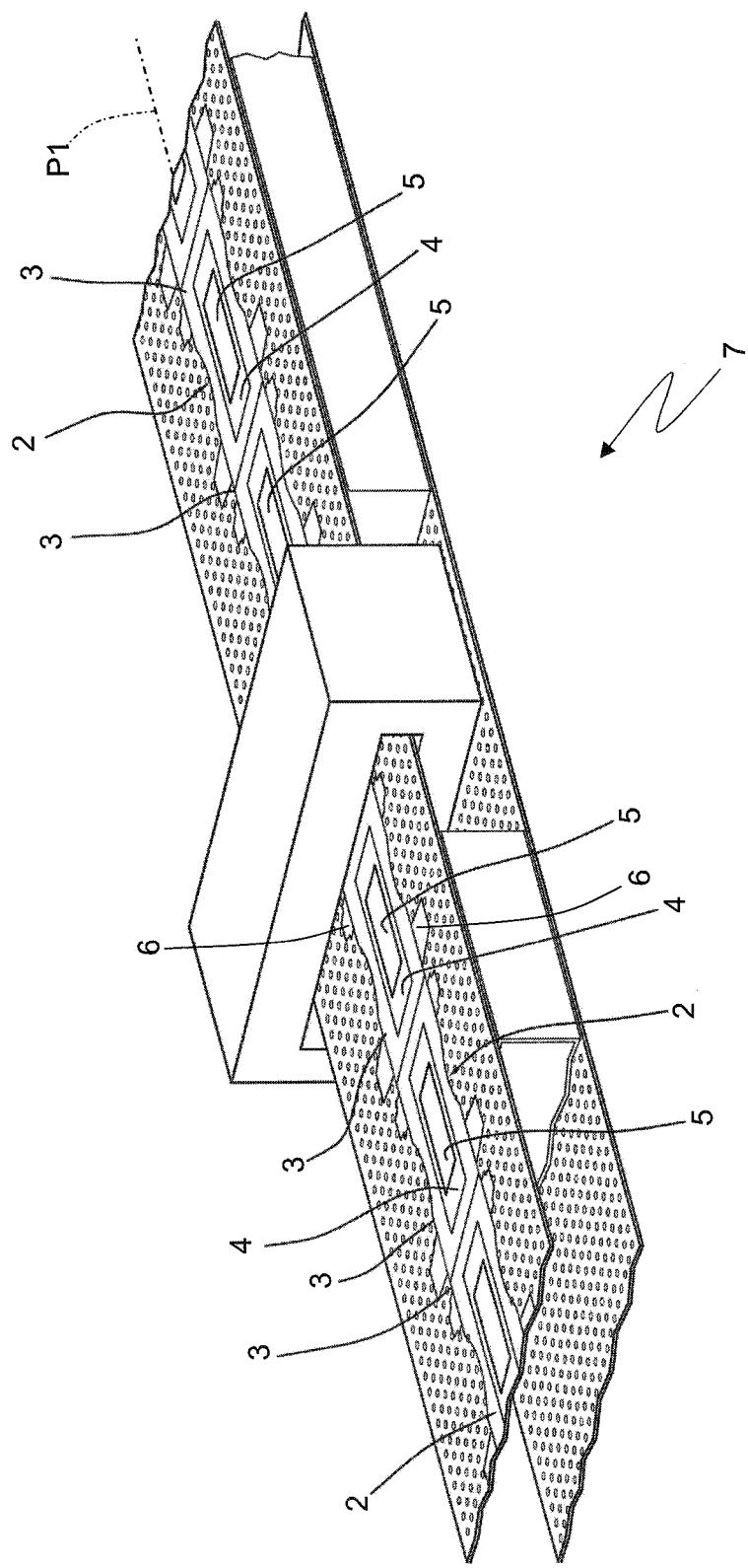
FIG. 2 is a perspective and schematic view of part of a feeding line of the maker machine of FIG. 1.

As illustrated in FIG. 2, each hygiene absorbent article 2 comprises a sheet 3 of impermeable material (e.g. polyethylene) and a sheet 4 of permeable material (for example, "non-woven fabric") between which an absorbent padding 5 is enclosed which forms the part of the hygiene absorbent article 2 used for absorbing organic liquids. The absorbent padding 5 is normally (but not necessarily) formed by a homogeneous mixture of natural fibrous material ("fluff") and superabsorbent polymer material ("SAP"). Furthermore, in order to increase the absorbent capacity, the padding 5 could also comprise a discrete layer of superabsorbent polymer material ("SAP") defining a further absorbent material; preferably, said superabsorbent polymer material is a granular superabsorbent polymer material. Each hygiene absorbent article 2 also comprises two pairs of lateral wings 6 which extend transversely from opposite sides of the hygiene absorbent article 2 and are adapted, in use, to overlap each other for closing the hygiene absorbent article 2 around the waist of the user.

As illustrated in FIG. 1, the maker machine 1 comprises a feeding line 7, which feeds, along a straight and horizontal forming path P1 at least one continuous strip of impermeable material, which is intended to define a succession of sheets 3 of impermeable material. Furthermore, the maker machine 1 comprises a plurality of operating units 8, which are arranged along the feeding line 7 (i.e. along the forming path P1) and feed the corresponding components of the hygiene absorbent articles 2 (i.e. the sheets 4 of permeable material, the padding 5 and the wings 6) to the sheets 3 of impermeable material.

Along the feeding line 7 (i.e. along the forming path P1), the first operating unit 8a is a forming and application unit 8 for a succession of absorbent padding 5. Downstream from the operating unit 8a additional operating units 8b and 8c are arranged which manufacture the accessories of the hygiene absorbent articles 2 (for example elastic bands, fecal barriers and lateral wings 6), and apply the accessories to the sheets 3 of impermeable material. Finally, at the end of the feeding line 7 (i.e. at the end of the forming path P1) an operating unit 8d is arranged, which applies the sheets 4 of permeable material over the sheets 3 of impermeable material so as to enclose between each sheet 3 of impermeable material and the corresponding sheet 4 of a permeable material an absorbent padding 5. Obviously the arrangement of the operating units 8 along the feeding line 7 (i.e. along the forming path P1) can be different.

Figure 3:
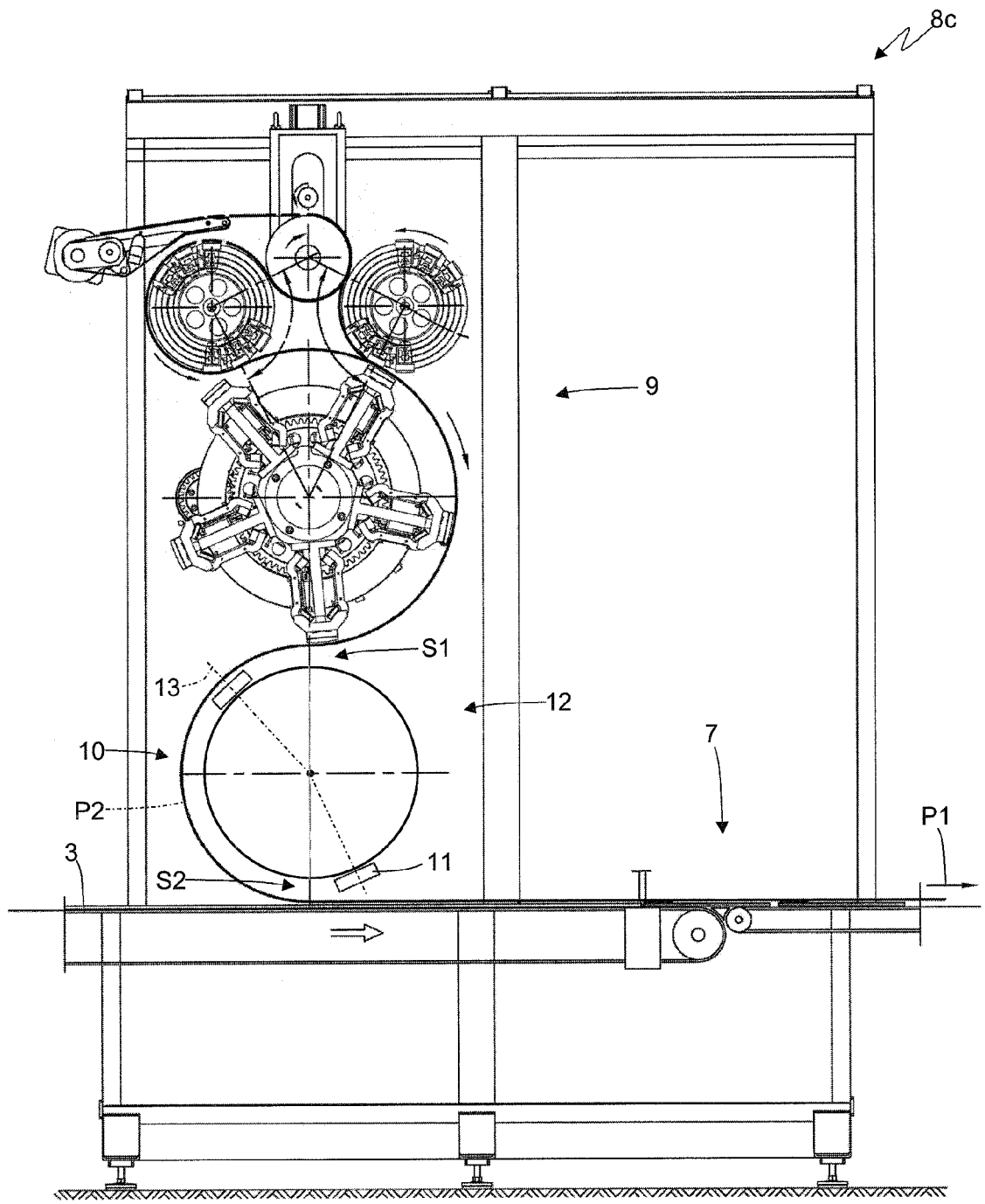
FIG. 3 is a schematic front view of an operating unit of the maker machine of FIG. 1.

As illustrated in FIG. 3, the operating unit 8c applies a succession of components (in particular the lateral wings 6) to the sheets 3 of impermeable material carried by the feeding line 7 along the forming path P1. The operating unit 8c comprises a processing device 9 which receives the components in succession and processes the components (in particular, performs the cutting of the components) and an application device 10, which receives the finished components from the processing device 9 and applies the components to the sheets 3 of impermeable material carried by the feeding line 7. The application device 10 comprises a plurality of sucking pick-up heads 11 (only two of which are illustrated in FIG. 3 for clarity) each adapted to receive, hold and subsequently apply a corresponding component, and a conveyor 12 which supports the sucking pick-up heads 11 and cyclically moves each sucking pick-up head 11 along a circular application path P2 that passes through a pick-up station S1 wherein the sucking pick-up head 11 receives a corresponding component from the processing device 9 and a release station S2, in which the sucking pick-up head 11 applies the component to a corresponding sheet 3 of impermeable material carried by the feeding line 7.

According to a preferred (but not binding) embodiment, each sucking pick-up head 11 is mounted to rotate upon itself around a rotation axis 13 arranged in a radial manner (i.e. perpendicular) to the application path P2. In use, between the pick-up station S1 and the release station S2 each sucking pick-up head 11 carrying a component performs a 90° rotation around the corresponding rotation axis 13 so as to change the orientation of the component carried by the sucking pick-up head 11; between the release station S2 and the pick-up station S1 each sucking pick-up head 11 devoid of component performs a counter-rotation (i.e. a rotation in the opposite direction) of 90° around the corresponding rotation axis 13 to return to the starting position before receiving a new component.

Figure 4:
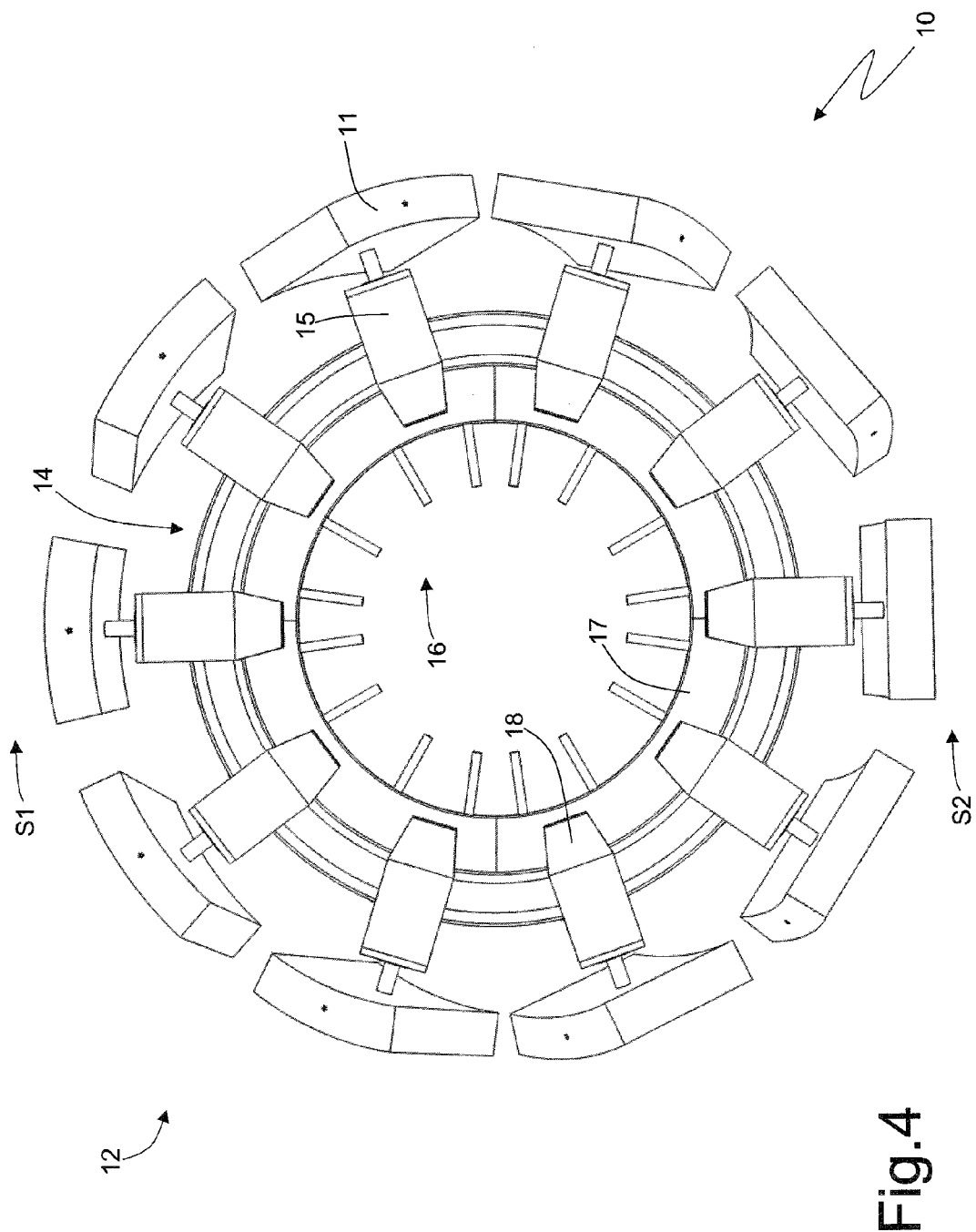
FIG. 4 is a front view of an application device of the operating unit of FIG. 3.

As illustrated in FIG. 4, the conveyor 12 comprises an annular guide 14 (i.e. closed in a loop upon itself) which is arranged in a fixed position along the application path P2; in particular, the annular guide 14 is formed by a single fixed rail (i.e. without movement) that is arranged along the application path P2. Furthermore, the conveyor 12 comprises a plurality of slides 15, each of which supports a corresponding sucking pick-up head 11 and is coupled to the guide 14 so as to freely slide along the guide 14. Finally, the conveyor 12 comprises a linear electric motor 16 which moves the slides 15 carrying the sucking pick-up heads 11 along the application path P2; the linear electric motor 16 comprises an annular stator 17 (i.e. a primary fixed one) which is arranged in a fixed position along the guide 14 and a plurality of mobile sliders 18 (i.e. secondary mobile ones), each of which is electro-magnetically coupled to the stator so as to receive, from the stator 17 a driving force and is rigidly connected to a corresponding slide 15.

The stator 17 of the electric linear motor 16 comprises a ferromagnetic armature having a series of slots housing windings adapted to be crossed by electrical currents variable over time to generate corresponding stator magnetic fields (variables in time); each slider 18 of the linear electric motor 16 comprises a ferromagnetic armature in which at least one permanent magnet is arranged, which generates a rotor magnetic field (constant in time) that interacts with the magnetic field of the stator to generate, on the slider 18, a driving force of electromagnetic source. In each slide 15, the slider 18 is mounted so as to be in close proximity (approximately 1-2 mm) with the stator 17 to minimize the air gap existing between the ferromagnetic armature of the slider 18 and the ferromagnetic armature of the stator 17.

A control device which drives the linear electric motor 16 by applying a variable voltage to the windings of the stator 17 is provided. Preferably, the control device uses a closed loop control system (that is, in feedback) to control the position of each slider 18 (therefore of each slide 15). Consequently, the control device must know in real time and with good precision the actual location of each slider 18 (therefore of each slide 15) along the application path P2; for this purpose, the control device can reconstruct the actual position of each slider 18 along the application path P2 by means of estimation algorithms based on electrical signals at the winding heads of the stator 17 or the control device can receive the detection of a specific position sensor which is arranged along the application path P2. For example, the position sensor comprises a measuring ring in magnetostrictive material that is arranged along the application path P2 and, for each slider 18, a corresponding permanent magnet that is arranged in proximity to the measuring ring.

Figure 6:
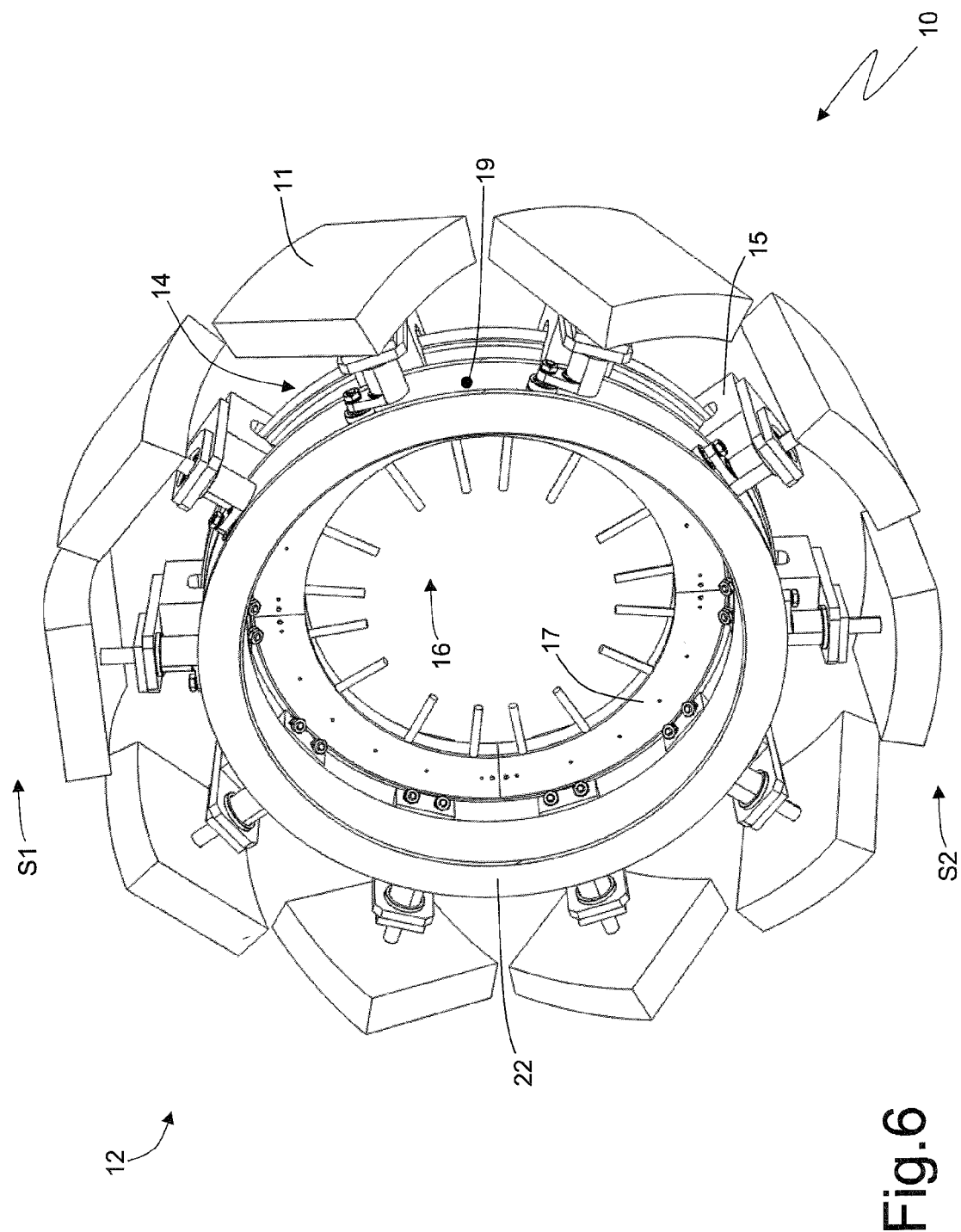
FIG. 6 is a rear perspective view of the application device of FIG. 4.
Figure 7:
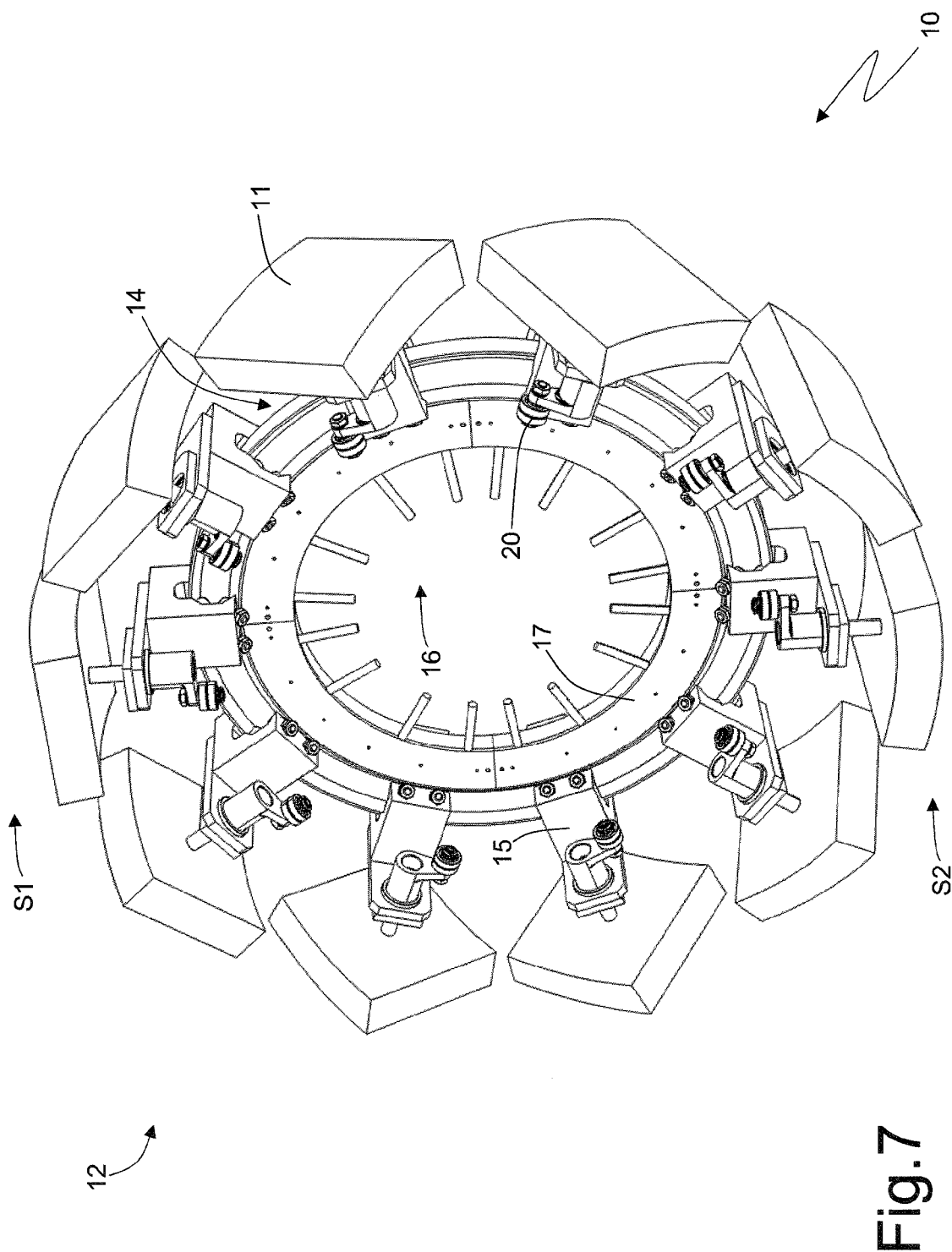
FIG. 7 is a rear perspective view and with the removal of parts for clarity of the application device of FIG. 4.

As previously mentioned, each sucking pick-up head 11 is mounted in a rotary manner on the corresponding slide 15 so as to rotate around a rotation axis 13; the conveyor 12 comprises a cam actuating system, so as to control the rotation of each sucking pick-up head 11 around the rotation axis 13. As illustrated in FIGS. 6 and 7, the cam actuating system comprises a cam 19 (not illustrated in FIG. 7) arranged in a fixed position beside to the guide 14 and along the application path P2 and, for each pick-up head 11, a corresponding cam follower roller 20 which is coupled to the cam 19 (i.e. it slides on the cam 19 to follow the profile of the cam 19) and is mechanically connected to the sucking pick-up head 11.

Figure 9:
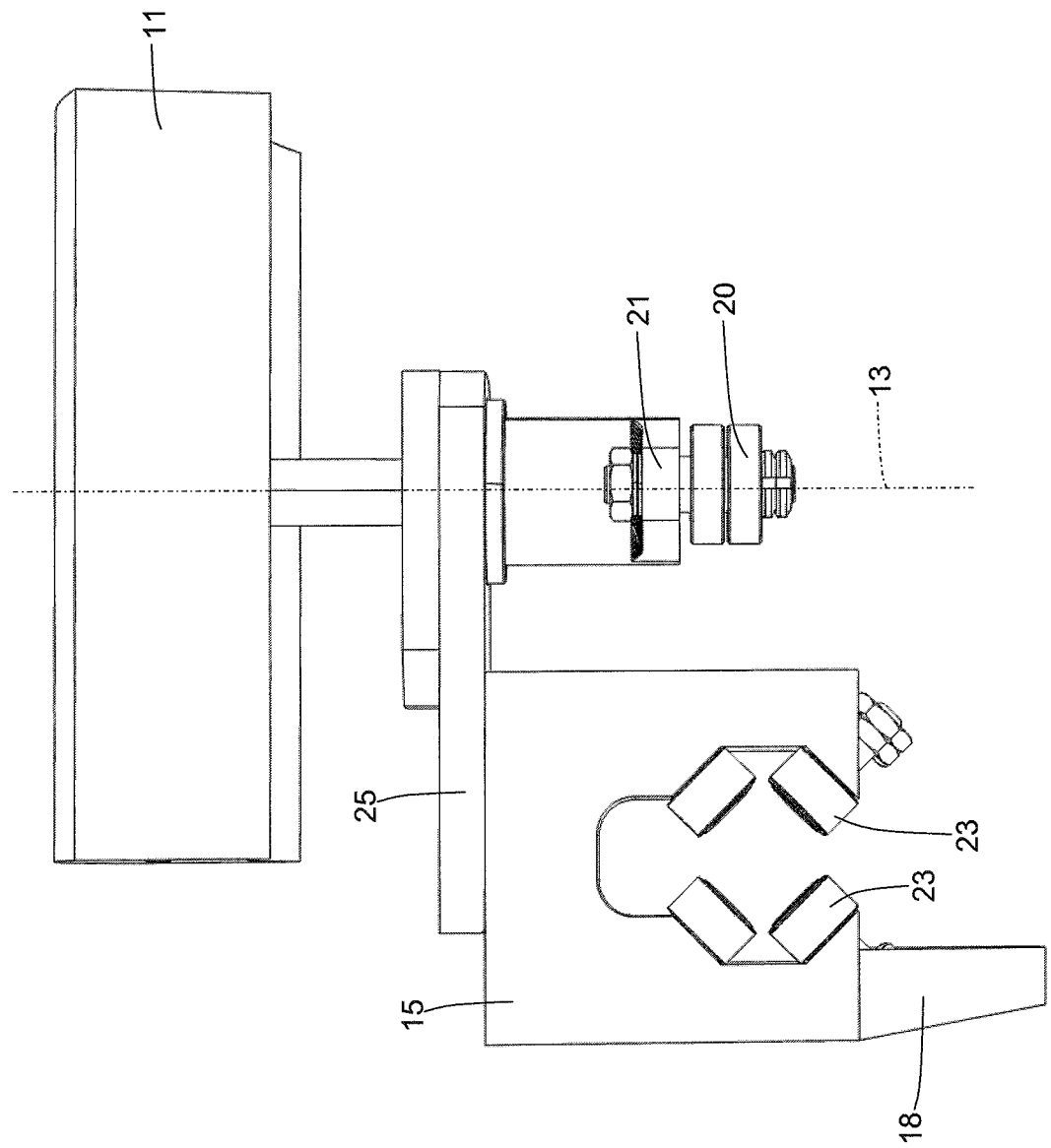
FIG. 9 is a side view of a mobile assembly of the application device of FIG. 4.
Figure 10:
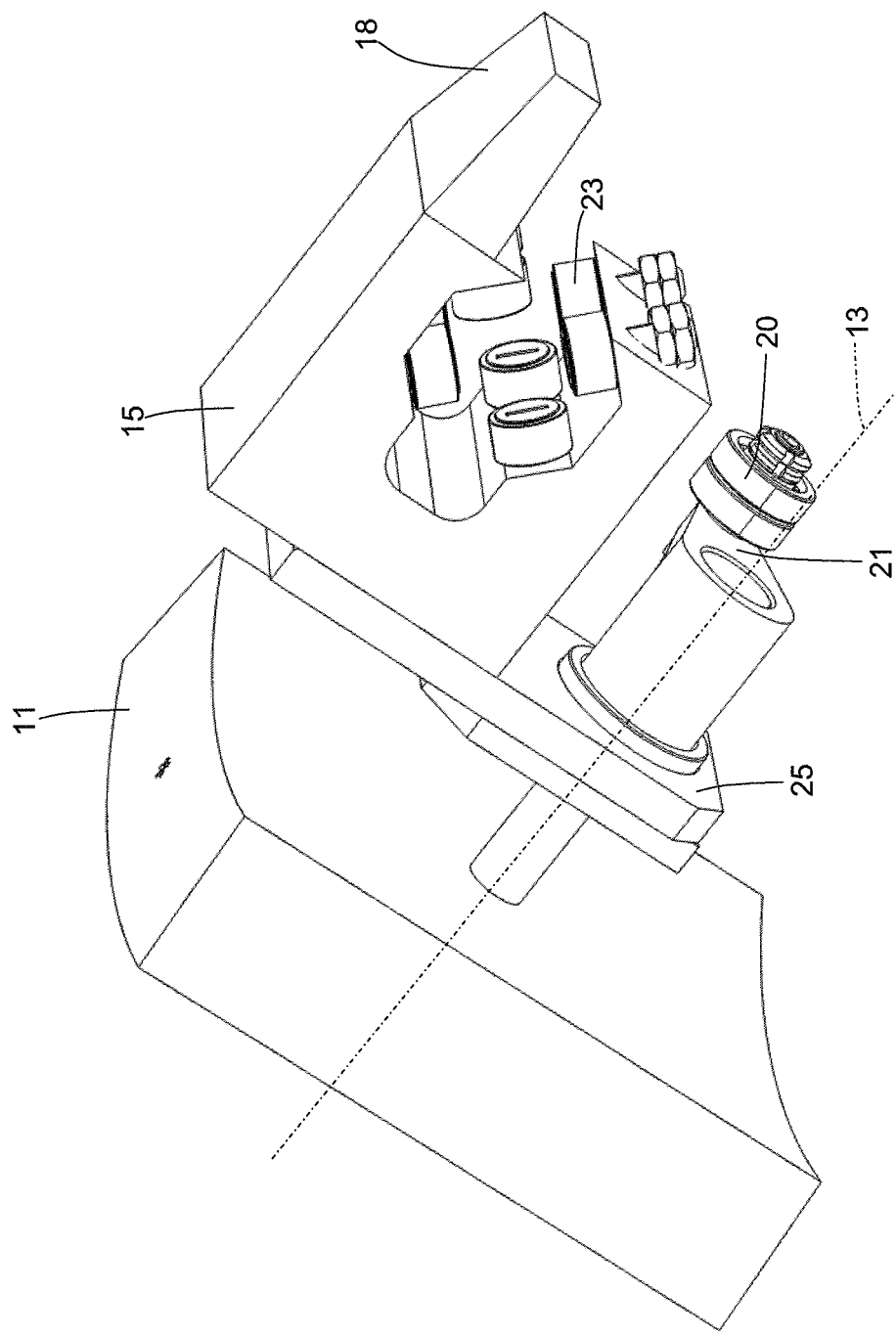
FIGS. 10 and 11 are two different perspective views of the mobile assembly of FIG. 9.
Figure 11:
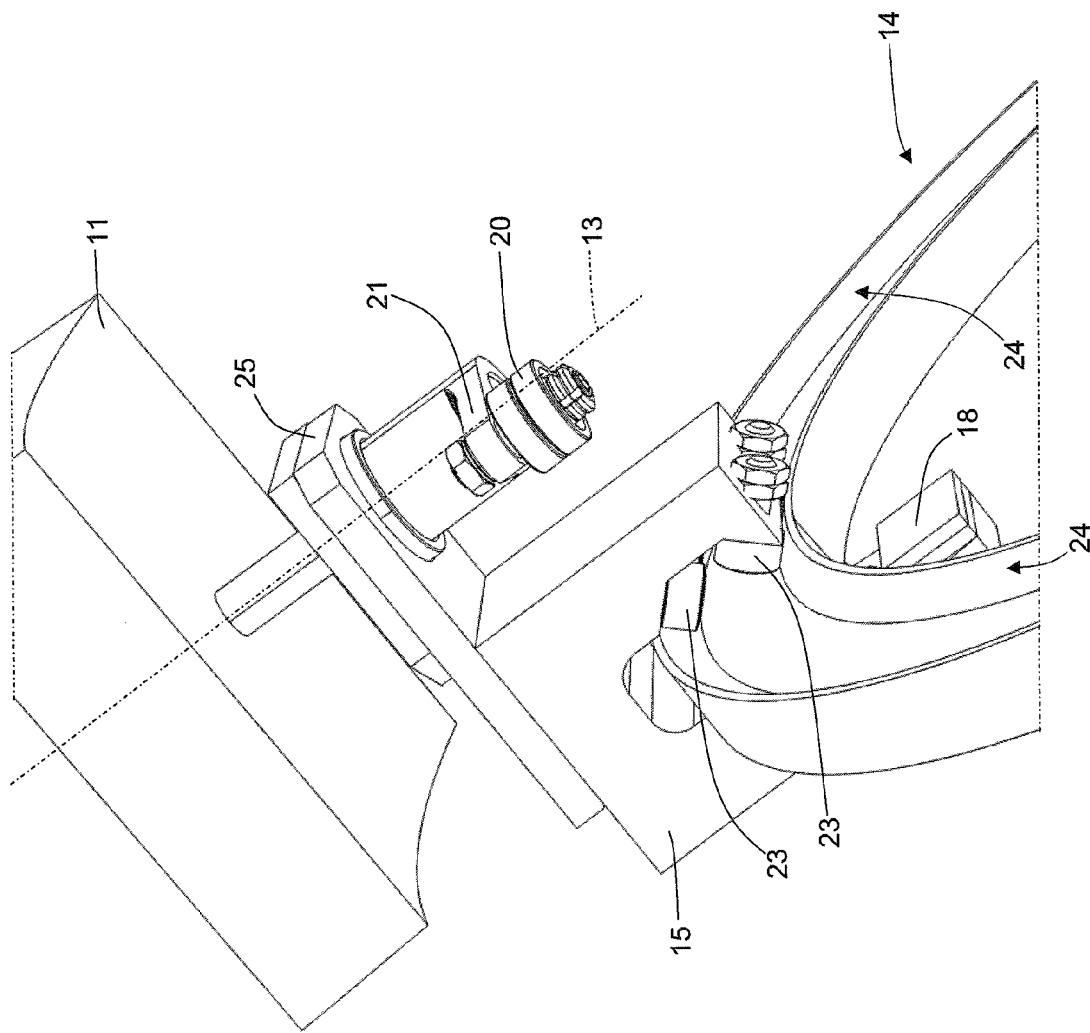
Figure 12:
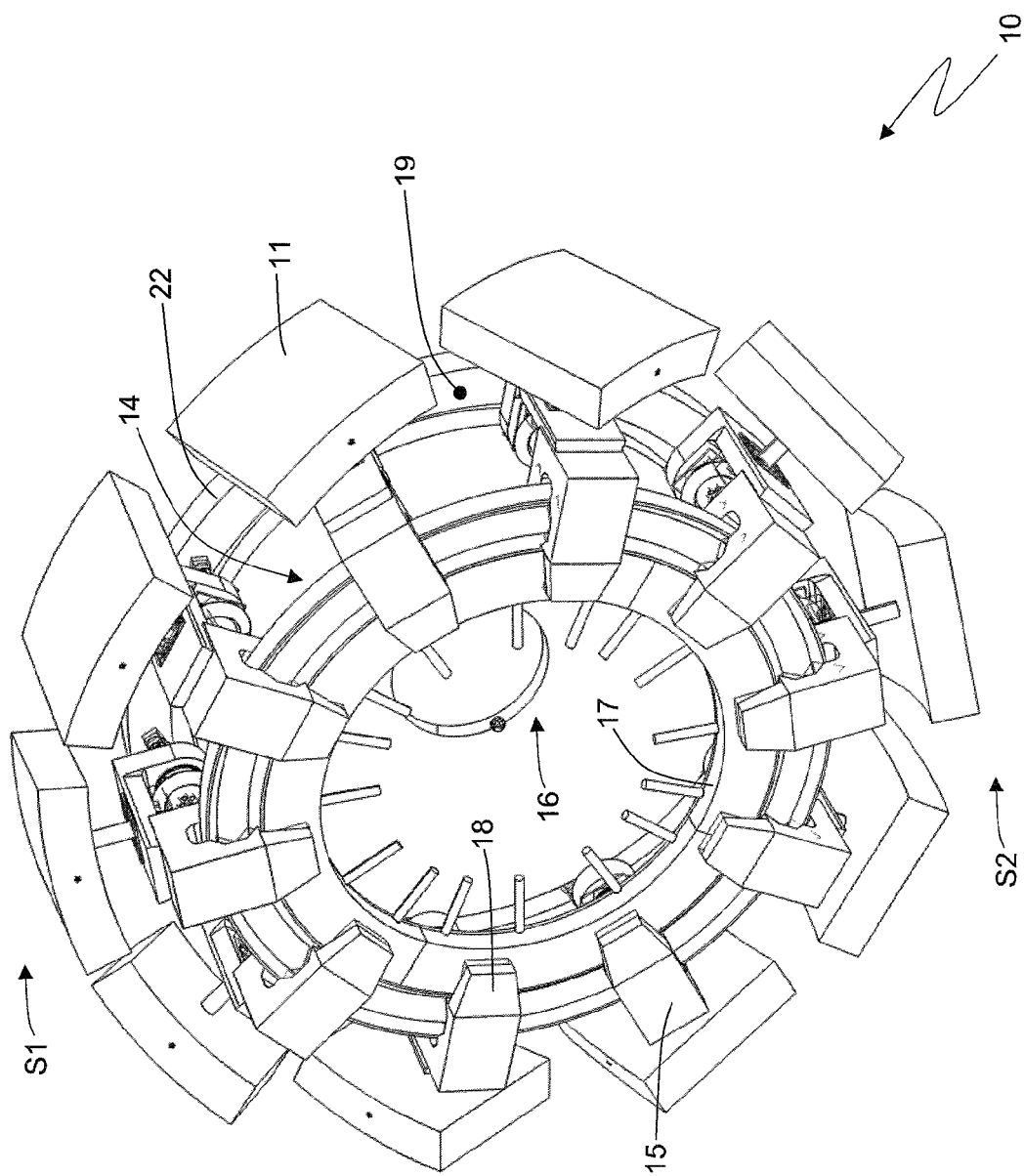
FIG. 12 is a front perspective view of an alternative of the application device of FIG. 4.
Figure 13:
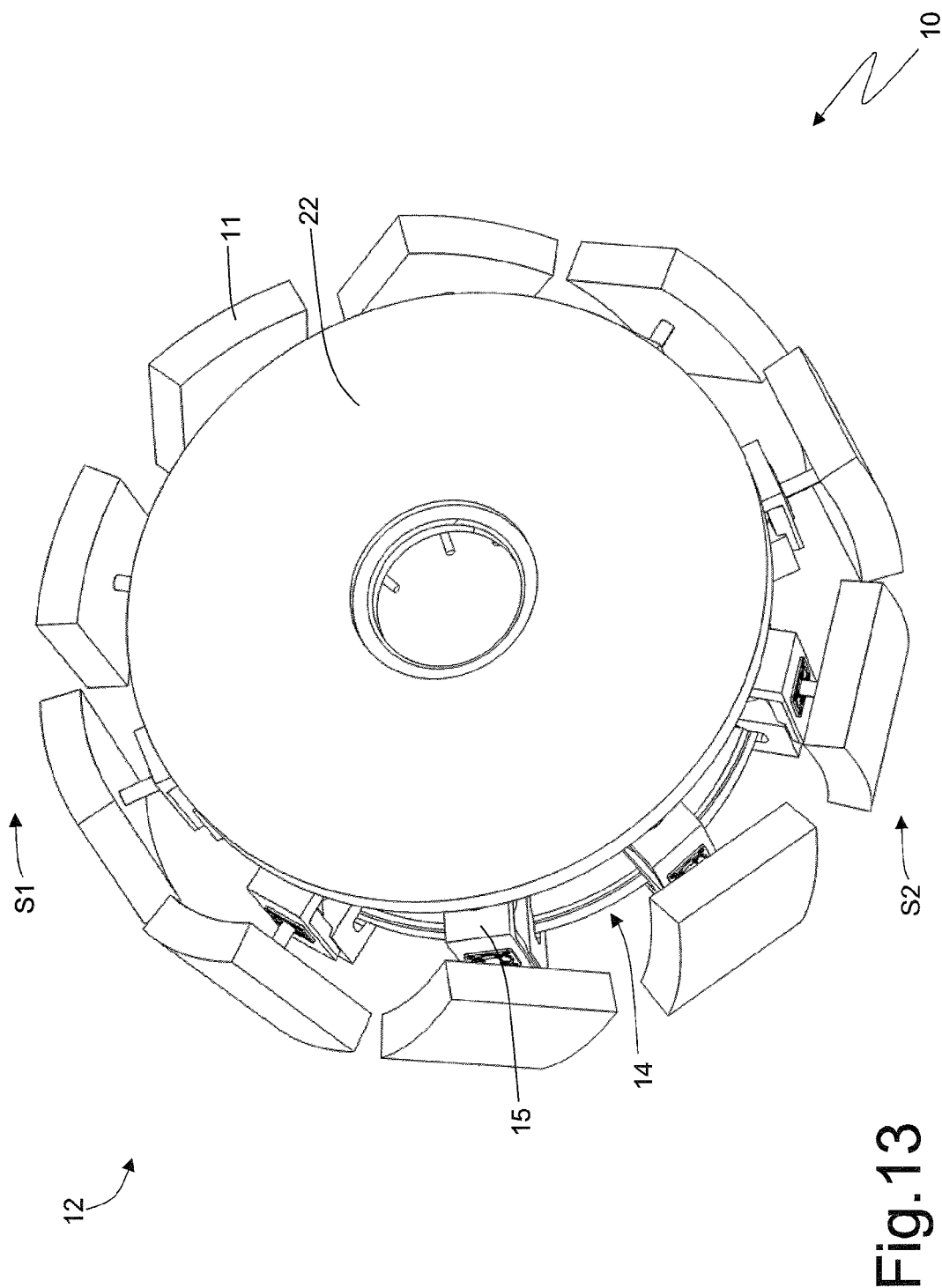
FIG. 13 is a rear perspective view of the application device of FIG. 12.
Figure 14:
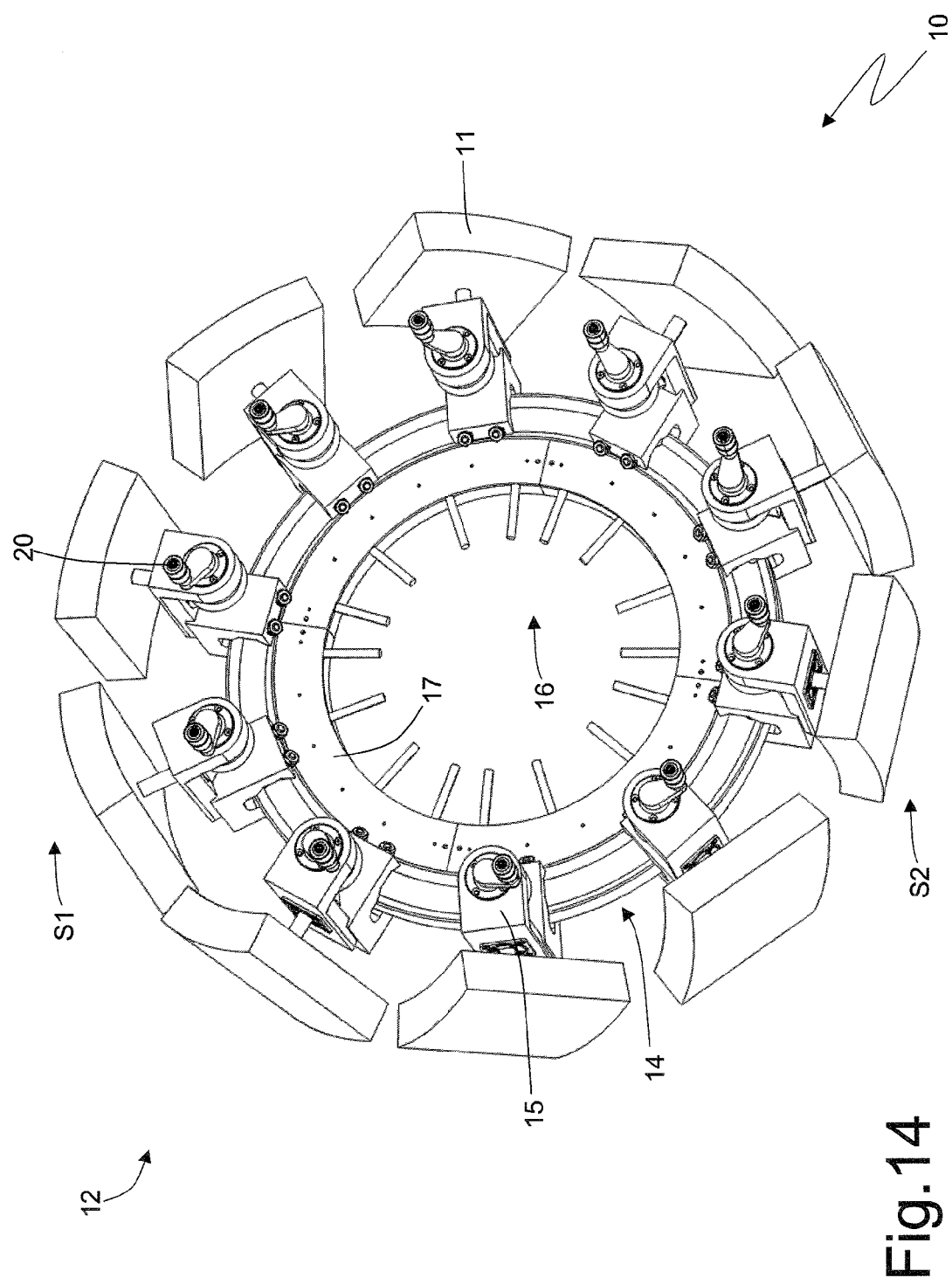
FIG. 14 is a rear perspective view and with the removal of parts for clarity of the application device of FIG. 12.

As illustrated in FIGS. 9, 10 and 11, in each slide 15 the cam follower roller 20 is oriented parallel to the rotation axis 13; furthermore, an actuation arm 21 is provided, which has a first end on which the cam follower roller 20 is mounted in a rotary manner and a second end which is angularly integral with the sucking pick-up head 11. In this embodiment, one end of each actuation arm 21 is directly bound to a shaft which supports the sucking pick-up head 11 so that the rotary movement of the actuation arm 21 becomes equal to a rotary movement of the sucking pick-up head 11.

Figure 5:
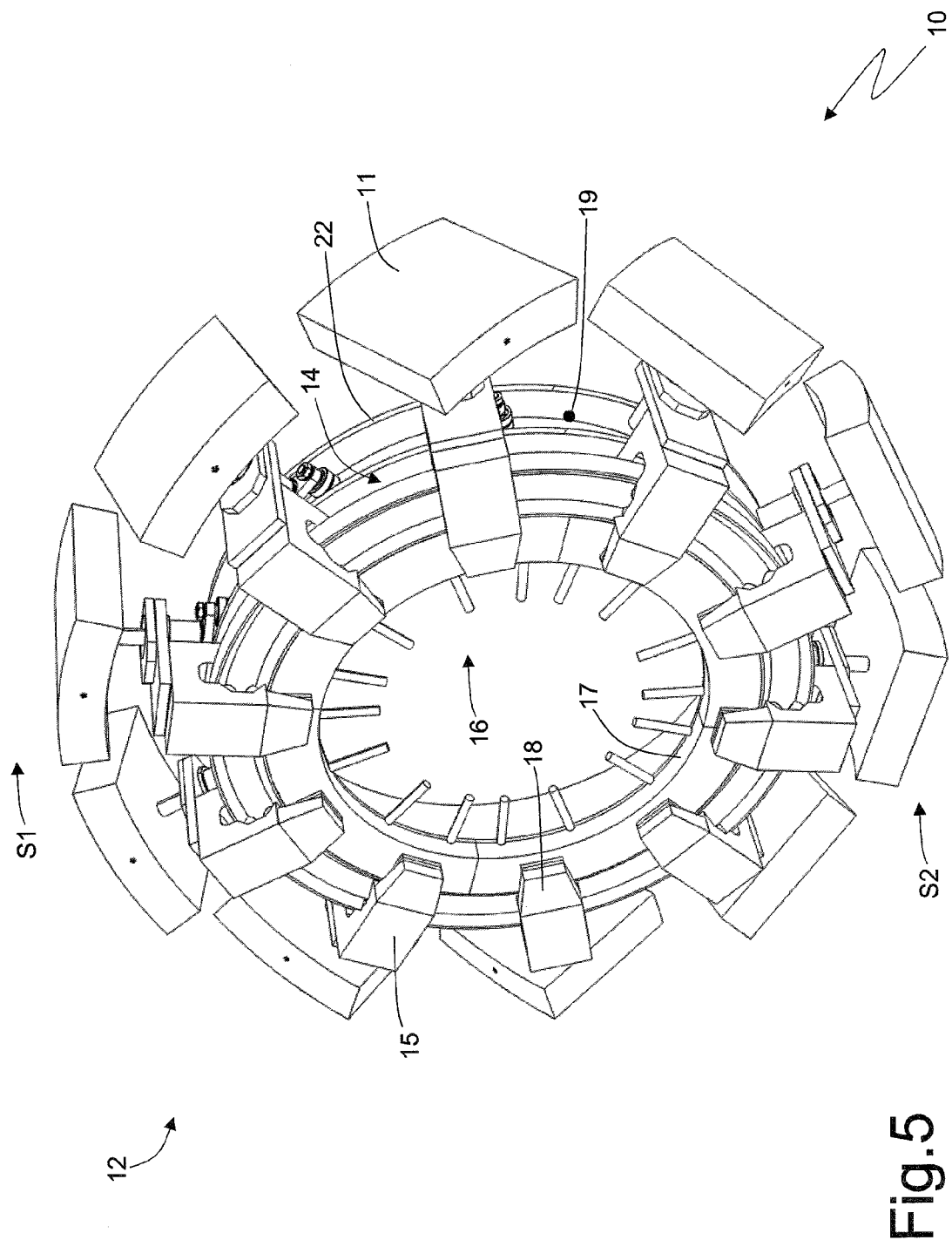
FIG. 5 is a front perspective view of the application device of FIG. 4.

According to a preferred embodiment illustrated in FIGS. 5 and 6, the conveyor 12 comprises a support element 22, which is arranged beside the guide 14 and in which the cam 19 is formed. In other words, the cam 19 is formed in the support element 22 which is at least initially separate and independent of the guide 14 and is arranged beside the guide 14.

As illustrated in FIGS. 9, 10 and 11, each slide 15 is "U"-shaped and embraces the guide 14 on both sides of the guide 14 (as illustrated in FIG. 11); in other words, each slide 15 has two legs which are facing and opposite to one another and embrace the guide 14 between one another (i.e. between the two legs of the slide 15 a chamber is defined which accommodates the guide 14). Each slide 15 supports a plurality of wheels 23, which are fitted on the slide 15 in an idle manner and roll along respective rolling surfaces 24 of the guide 14; in particular, each leg of the slide 15 supports two pairs of wheels 23 (in each pair of wheels 23 the two wheels 23 are arranged side by side, whereas the two pairs of wheels 23 of a same leg of the slide 15 are mutually opposite and oriented perpendicularly with respect to one another). On each side the guide 14 comprises a pair of rolling surfaces 24 (illustrated in FIGS. 8 and 11), which are arranged at a given distance from one another, are oriented perpendicular one with respect to the other, and are coupled to corresponding wheels 23 of the slide 15. The presence of the wheels 23 allows each slide 15 to slide along the guide 24 with a very low friction and at the same time ensures a transverse containment of the slide 15; i.e. each slide 15 can only slide along the guide 24 without making any movement perpendicular to the guide 24.

As illustrated in FIGS. 9, 10 and 11, each slide 15 is provided with a bracket 25, which projects from the slide 15 and supports the sucking pick-up head 11; in particular, the end of the bracket 25 protruding from the slide 15 has a through hole inside which a bearing is housed which carries a shaft supporting the corresponding sucking pick-up head 11.

Figure 8:
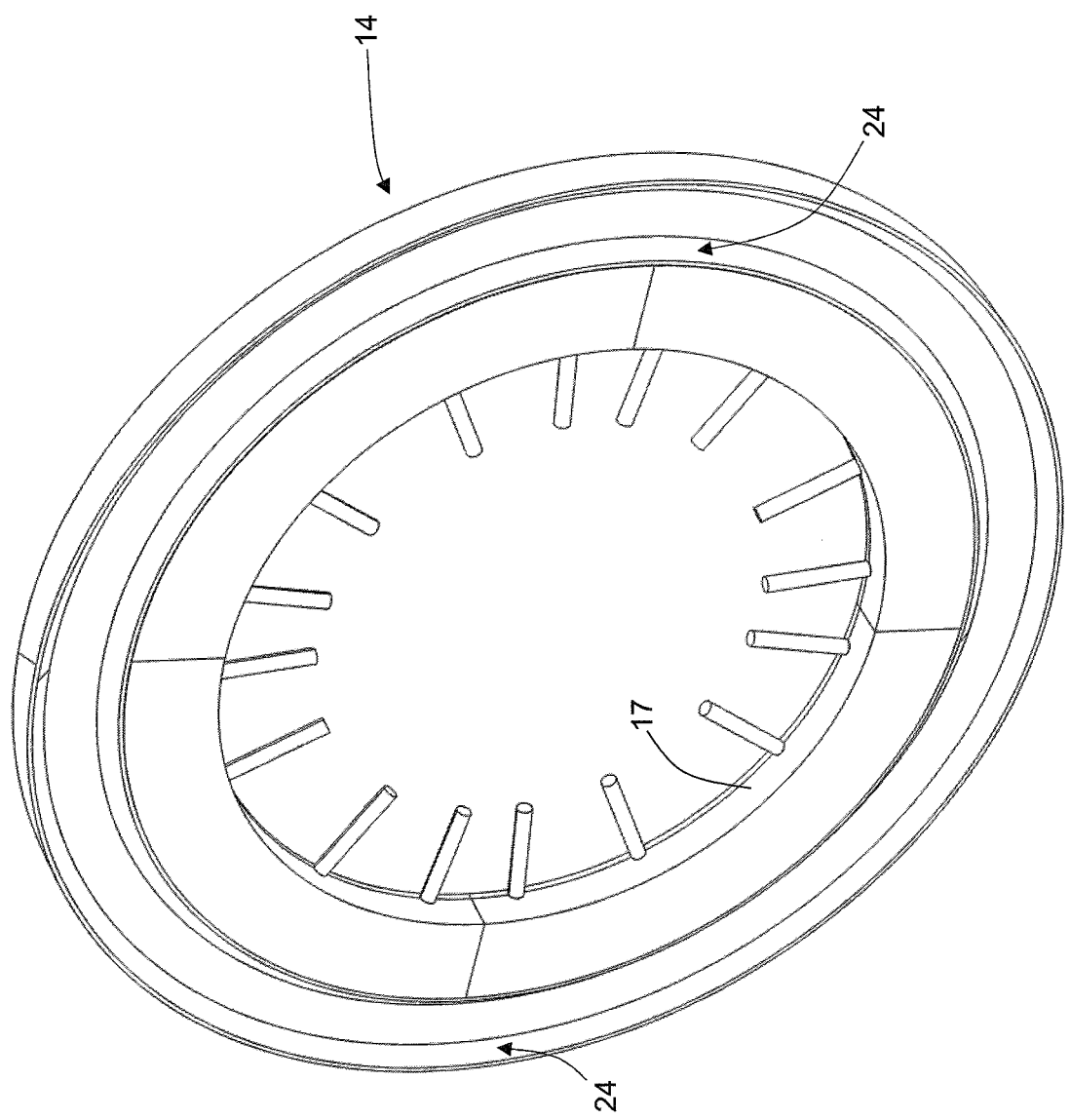
FIG. 8 is a front perspective view of a fixed guide and of a stator of a linear electric motor of the application device of FIG. 4.

As illustrated more clearly in FIG. 8, the stator 17 of the linear electric motor 16 is arranged coplanar with the guide 14 and inside the guide 14. In other words, the stator 17 of the linear electric motor 16 and the guide 14 are arranged on a same plane and one inside the other; in this way, the stator of the linear electric motor 16 can be mechanically connected (typically by means of screws) to the guide 14. According to a preferred, but not binding, embodiment, the stator 17 of the linear electric motor 16 is divided into different sectors (four in FIG. 8, but can be more or less) arranged one following the other along the guide 14. The individual sectors of the stator 17 are mechanically and electrically independent, i.e. each sector of the stator 17 is electrically powered by its own driving device that is exclusively dedicated to its own sector (therefore is different and separate from the driving devices of the other sectors); obviously a central control unit is provided which controls in a coordinated manner the four driving devices for moving the slides 15 (therefore the corresponding sucking pick-up heads 11) along the application path P2 according to the desired law of motion.

Figure 15:
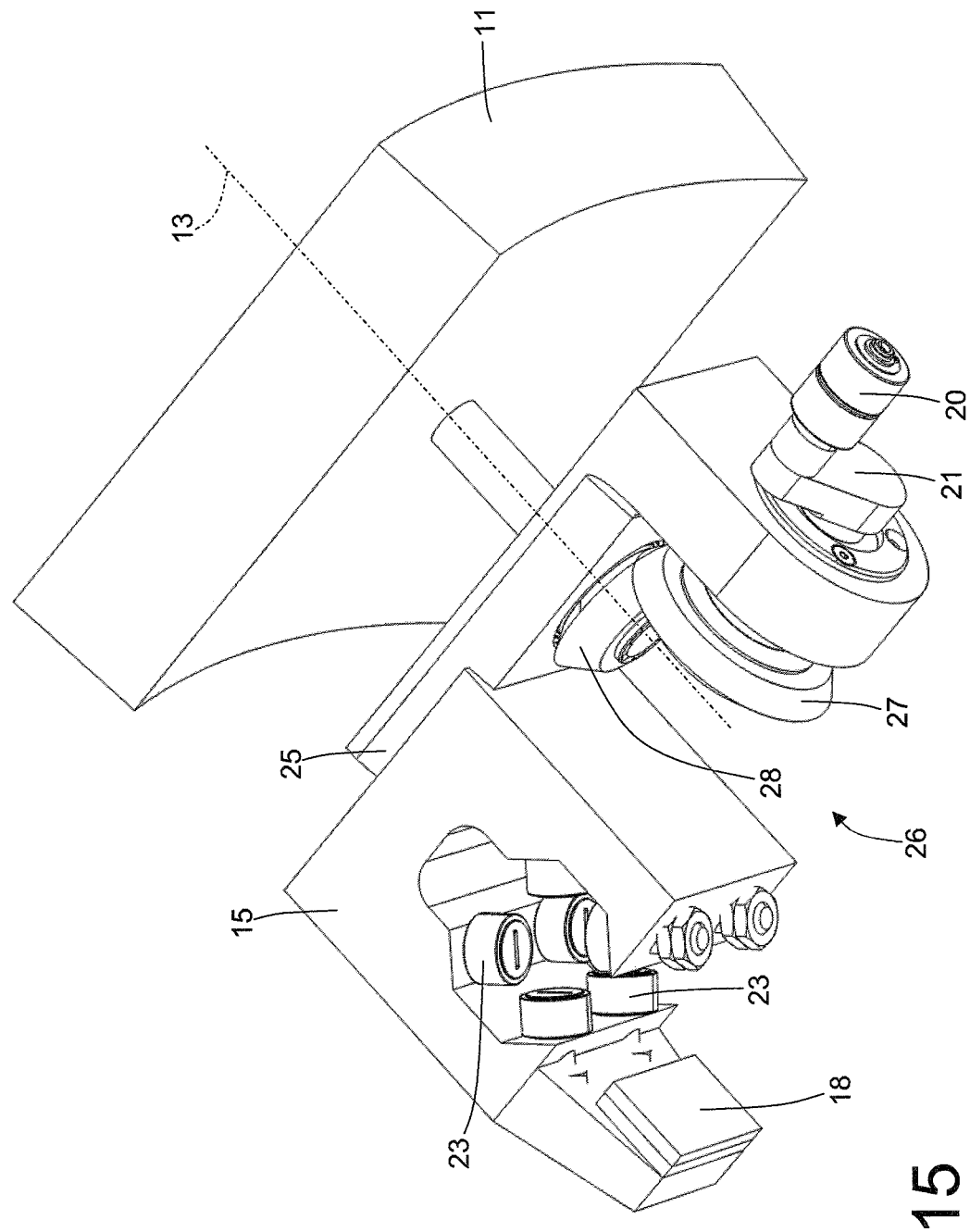
FIG. 15 is a perspective view of a mobile assembly of the application device of FIG. 12.
Figure 16:
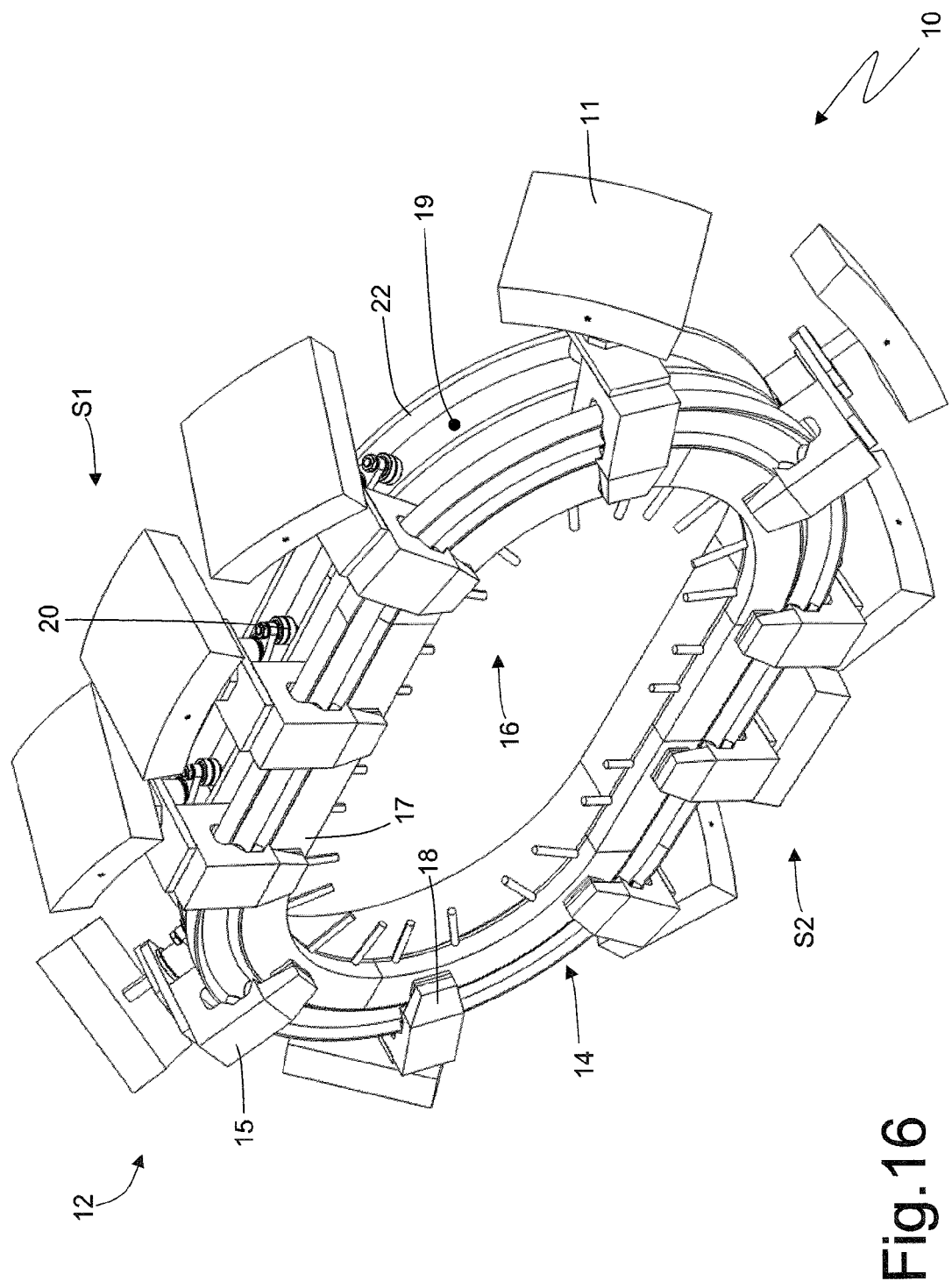
FIG. 16 is a front perspective view of a different embodiment of the application device of FIG. 4.
Figure 17:
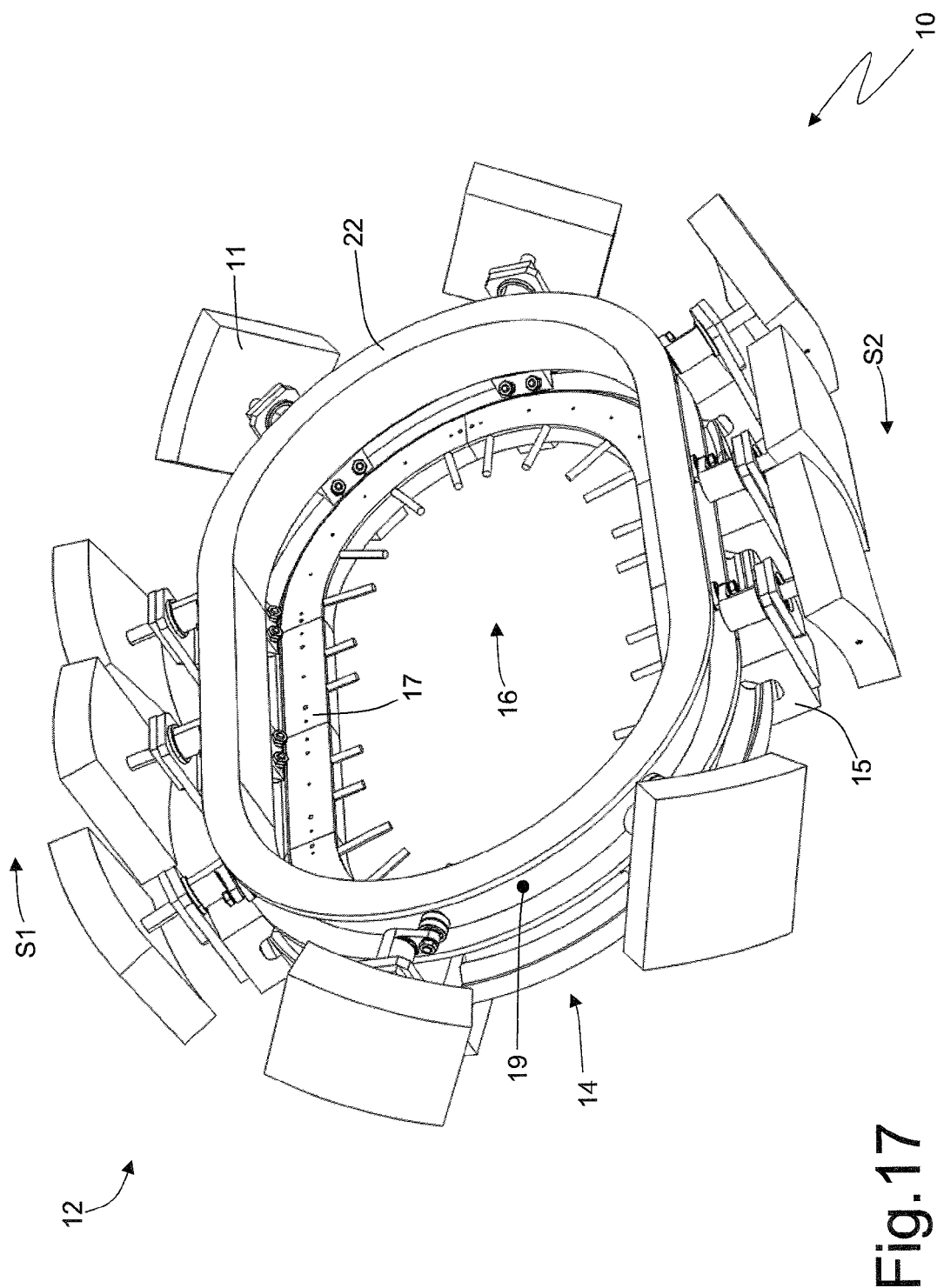
FIG. 17 is a rear perspective view of the application device of FIG. 16.
Figure 18:
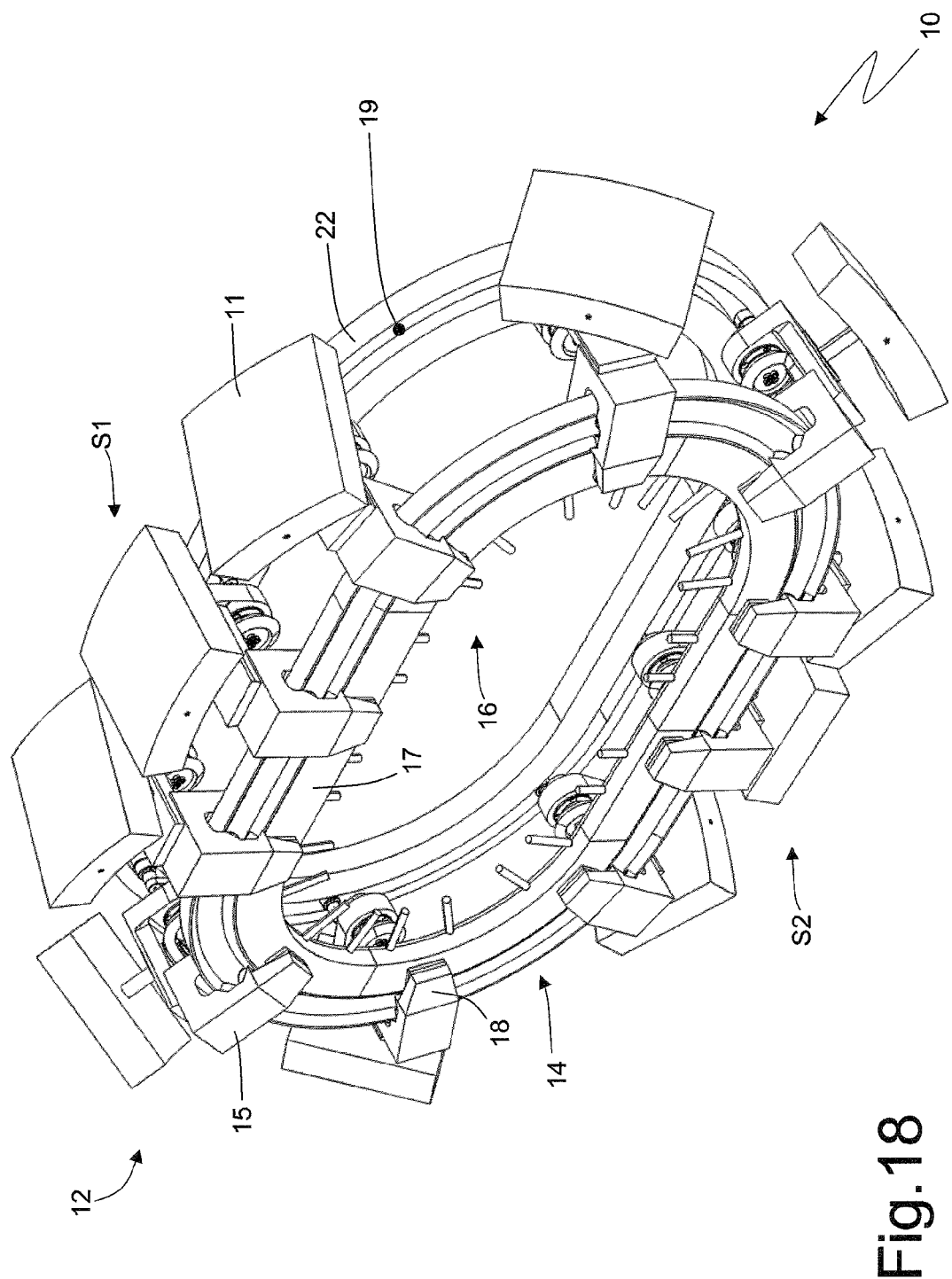
FIG. 18 is a front perspective view of a different embodiment of the application device of FIG. 12.
Figure 19:
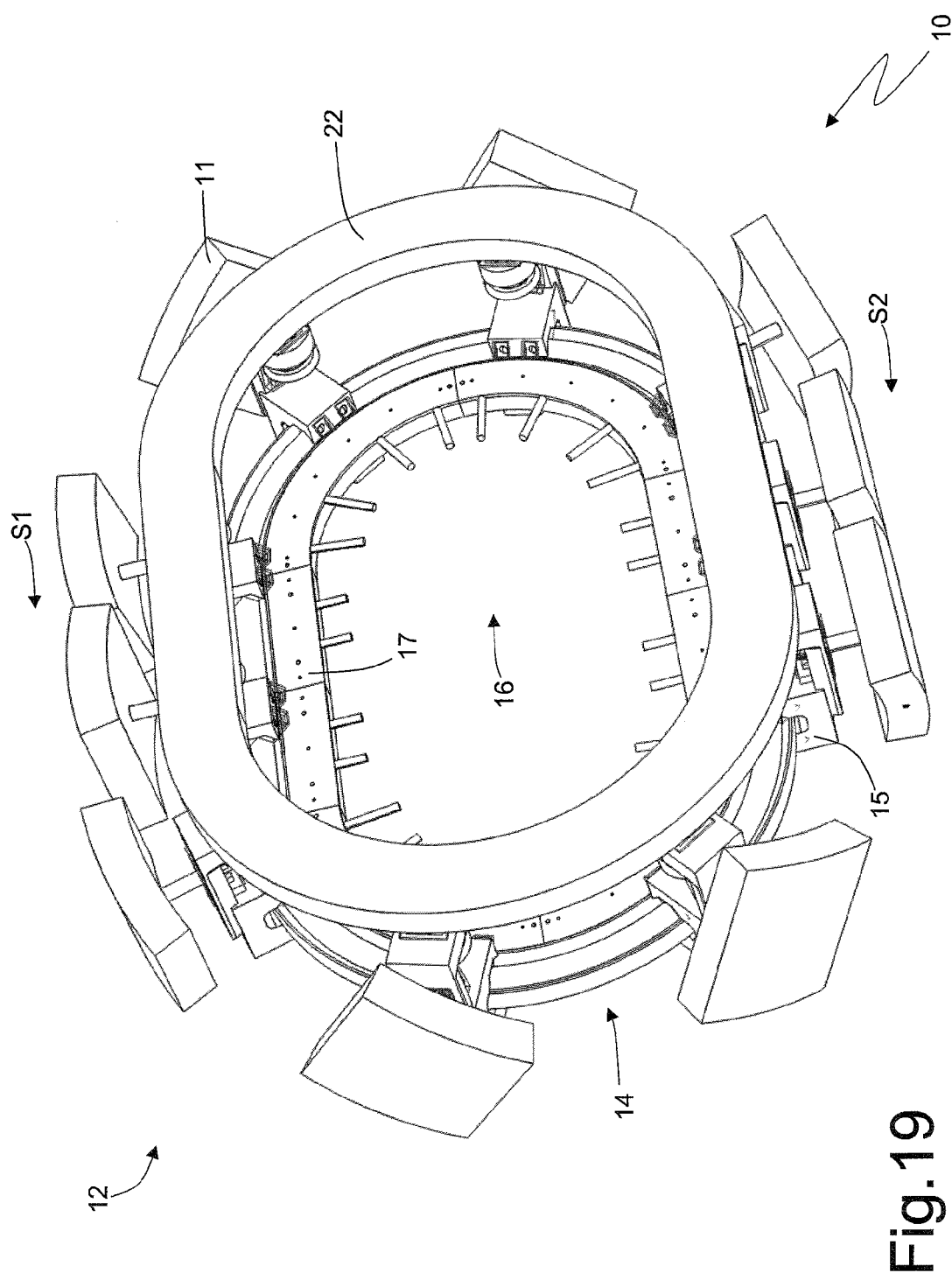
FIG. 19 is a rear perspective view of the application device of FIG. 18.

In the embodiment illustrated in FIGS. 4-11, the cam follower rollers 20 are oriented parallel to the corresponding rotation axes 13 (as clearly illustrated in FIGS. 9, 10 and 11); in the alternative illustrated in FIGS. 12-15, the cam follower rollers 20 are oriented perpendicular to the corresponding rotation axes 13 (as clearly illustrated in FIG. 15). As illustrated in FIG. 15, in each slide 15 the actuation arm 21 has a first end, on which the cam follower roller 20 is fitted in a rotary manner and a second end, which is mechanically connected to the sucking pick-up head 11 by means of a mechanical transmission system 26. In the preferred, but not limiting, embodiment illustrated in FIG. 15, the mechanical transmission system 26 comprises a gear wheel 27 angularly integral with the actuation arm 21 and a gear wheel 28 which is angularly integral with the sucking pick-up head 11 (in particular is keyed to a shaft which supports the sucking pick-up head 11), meshes with the gear wheel 27, and is oriented perpendicular to the gear wheel 27.

According to a possible embodiment, each slide 15 receives the suction from the guide 14: on an outer surface of the guide 14 a chamber is formed which communicates on the inside with a suction source and is open on the outside towards the slide 15; therefore each slide 15 imparts suction to the corresponding sucking pick-up head 11 by means of inner ducts provided with a rotary pneumatic joint at the shaft which supports the sucking pick-up head 11 or by means of a flexible outer tube which is able to follow the 90° rotation of the sucking pick-up head 11 around the rotation axis 13.

In the embodiments illustrated in FIGS. 1-15, the application path P2 is circular; in alternative embodiments illustrated in FIGS. 16-19, the application path P2 has an oval shape having two straight sections parallel and opposite one with respect to the other which are connected by two semicircular sections opposite one with respect to the other. In the embodiment illustrated in FIGS. 16 and 17, the cam follower rollers 20 are oriented parallel to the corresponding rotation axes 13 (similarly to the embodiment illustrated in FIGS. 4-11), while in the embodiment illustrated in FIGS. 18 and 19, the cam follower rollers 20 are oriented perpendicular to the corresponding rotation axes 13 (similarly to the embodiment illustrated in FIGS. 12-15). The oval shaped application path P2 allows to lengthen the release station S2 as each sucking pick-up head 11 can remain parallel to and facing the feeding line 7 for a particularly long section of the application path P2; in this way, the application of the finished components to the sheets 3 of impermeable material carried by the feeding line 7 can take place in a more accurate and precise manner even when operating at high hourly productivity.

In use, the linear electric motor 16 is able to control the movement of each slide 15 (therefore of each sucking pick-up head 11) along the guide 14 (i.e. along the application path P2) in a completely autonomous and independent manner of the other slides 15 (therefore of the other sucking pick-up heads 11); accordingly, each slide 15 (therefore each sucking pick-up head 11) is coupled to the guide 14 so as to freely slide along the guide 14 with a law of motion completely independent of the other slides 15 (therefore of the other sucking pick-up heads 11). The law of motion of each slide 15 (therefore of each sucking pick-up head 11) depending solely on the software control mode of the stator 17 of the linear electric motor 16; therefore, a change in the laws of motion of the slides 15 (therefore of the sucking pick-up heads 11) is done only by acting on the control software of the stator 17 of the linear electric motor 16.

In the embodiments illustrated in the attached figures, the stator 17 of the linear electric motor 16 is arranged inside the guide 14, i.e. the stator 17 of the linear electric motor 16 is arranged in contact with an inner surface of the guide 14. According to a different embodiment not illustrated, the stator 17 of the linear electric motor 16 is arranged outside the guide 14. i.e. the stator 17 of the linear electric motor 16 is arranged in contact with an outer surface of the guide 14. According to a further embodiment not illustrated, the stator 17 of the linear electric motor 16 is arranged beside the guide 14, i.e. the stator 17 of the linear electric motor 16 is arranged in contact with a lateral surface of the guide 14. In addition, in the embodiments illustrated in the accompanying figures, the stator 17 of the linear electric motor 16 is arranged coplanar with the guide 14, i.e. the lying plane of the stator 14 is parallel and coincident with the lying plane of the guide 14. According to a different embodiment not illustrated, the lying plane of the stator 14 is perpendicular to the lying plane of the guide 14. According to a further embodiment not illustrated, the lying plane of the stator 14 is parallel to the lying plane of the guide 14 but not coincident with the lying plane of the guide 14. In the embodiments illustrated in the attached figures, the stator 17 of the linear electric motor 16 is arranged inside the guide 14 (in contact with an inner surface of the guide 14) and the stator 17 of the linear electric motor 16 is arranged coplanar with the guide 14 (i.e. the lying plane of the stator 14 is parallel and coincident with the lying plane of the guide 14). According to a different embodiment not illustrated, the stator 17 of the linear electric motor 16 is arranged outside the guide 14 (in contact with an outer surface of the guide 14) and the lying plane of the stator 14 is perpendicular to the plane of the guide 14. According to a further embodiment not illustrated, the stator 17 of the linear electric motor 16 is arranged beside the guide 14 (in contact with a lateral surface of the guide 14) and the lying plane of the stator 14 is parallel to the lying plane of the guide 14 but not coincident with the lying plane of the guide 14.

In the embodiment described above, the components that are applied to the application device 10 provided with the conveyor 12, with the linear electric motor 16, are the wings 6; it is evident that the application device 10 of the conveyor 12 provided with the linear electric motor 16 can also be used to apply any other type of component.

The maker machine 1 described above has numerous advantages.

First, in the application device 10 a format change operation, i.e. an operation that changes the maker machine 1 in order to vary the type of hygiene absorbent articles 2 that are made, is extremely simple and fast, as the only physical change that can be required is the replacement of the sucking pick-up heads 11, whereas the law of motion of the sucking pick-up heads 11 (i.e. of the slides 15) is modified thanks to an intervention on the control software. In other words, changing the law of motion of the sucking pick-up heads 11 does not require the replacement of any mechanical components, but takes place completely by way of software.

Furthermore, the conveyor 9 of the application device 10 is easy and inexpensive to produce as from the mechanical point of view is relatively simple and consists of a limited number of components.

The invention claimed is:

1. A maker machine (1) to manufacture hygiene absorbent articles (2); the maker machine (1) comprises:
 a feeding line (7), which feeds, along a straight and horizontal forming path (P1), a continuous strip of impermeable material, which is intended to define a succession of sheets (3) of impermeable material; and
 at least one operating unit (8), which is arranged along the forming path (P1) and feeds a corresponding component of the hygiene absorbent articles (2) to the sheets (3) of impermeable material carried by the feeding line (7);
 wherein the operating unit (8) comprises a processing device (9), which receives the components in succession and processes the components, and an application device (10), which receives the finished components from the processing device (9) and applies the components to the sheets (3) of impermeable material; and
 wherein the application device (10) comprises at least one sucking pick-up head (11) and a conveyor (12) to cyclically move the pick-up head (11) along an annular application path (P2), which extends through a pick-up station (S1), where the pick-up head (11) receives a corresponding component from the processing device (9), and a release station (S2), where the pick-up head (11) applies the component to a corresponding sheet (3) of impermeable material carried by the feeding line (7);
 wherein the conveyor (12) comprises:
 an annular guide (14), which is arranged in a fixed position along the application path (P2);
 a slide (15), which supports in a rotary manner the sucking pick-up head (11) such that the sucking pick-up head (11) rotates around a rotation axis (13) and is coupled to the guide (14) so as to freely slide along the guide (14);
 a linear electric motor (16), which comprises a stator (17), which is arranged in a fixed position along the guide (14), and a mobile slider (18), which is electro-magnetically coupled to the stator (17) so as to receive, from the stator (17), a driving force and is rigidly connected to the slide (15); and
 an actuation system to control the rotation of the sucking pick-up head around the rotation axis (13).

2. A maker machine (1) according to claim 1, wherein the actuation system comprises:
 a cam (19), which is arranged in a fixed position beside the guide (14) and long the application path (P2); and
 a cam follower roller (20), which is coupled to the cam (19) and is mechanically connected to the sucking pick-up head (11).

3. A maker machine (1) according to claim 2, wherein:
 the cam follower roller (20) is oriented parallel to the rotation axis (13); and
 an actuation arm (21) is provided, which has a first end, on which there is fitted, in a rotary manner, the cam follower roller (20), and a second end, which is angularly integral with the sucking pick-up head (11).

4. A maker machine (1) according to claim 2, wherein:
 the cam follower roller (20) is oriented perpendicular to the rotation axis (13); and
 an actuation arm (21) is provided, which has a first end, on which there is fitted, in a rotary manner, the cam follower roller (20), and a second end, which is mechanically connected to the sucking pick-up head (11) by means of a mechanical transmission system (26).

5. A maker machine (1) according to claim 4, wherein the mechanical transmission system (26) comprises a first gear wheel (27), which is angularly integral with the actuation arm (21), and a second gear wheel (28), which is angularly integral with the sucking pick-up head (11), meshes with the first gear wheel (27), and is oriented perpendicular to the first gear wheel (27).

6. A maker machine (1) according to claim 2, wherein the conveyor (12) comprises a support element (22), which is arranged beside the guide and in which the cam (19) is obtained.

7. A maker machine (1) according to claim 1, wherein the slide (15) is 'U'-shaped and embraces the guide (14) on both sides of the guide (14).

8. A maker machine (1) according to claim 7, wherein the slide (15) supports a plurality of wheels (23), which are fitted on the slide (15) in an idle manner and roll along respective rolling surfaces (24) of the guide (14).

9. A maker machine (1) according to claim 8, wherein, on each side, the guide (14) comprises a pair of rolling surfaces (24), which are arranged at a given distance from one another, are oriented perpendicular to one another, and are coupled to corresponding wheels (23) of the slide (15).

10. A maker machine (1) according to claim 1, wherein a bracket (25) is provided, which projects from the slide (15) and supports the sucking pick-up head (11).

11. A maker machine (1) according to claim 1, wherein the stator (17) is coplanar with the guide (14) and is arranged on the inside of the guide (14).

12. A maker machine (1) according to claim 1, wherein the conveyor (12) comprises a plurality of slides (15), each of which supports a corresponding sucking pick-up head (11) and is coupled to the guide (14) so as to freely slide along the guide (14) with a law of motion that is completely independent of the other slides (15).

13. A maker machine (1) according to claim 1, wherein the stator (17) of the linear electric motor (16) is divided into different sectors arranged one following the other along the guide (14).

14. A maker machine (1) to manufacture hygiene absorbent articles (2); the maker machine (1) comprises:
- a feeding line (7), which feeds, along a straight and horizontal forming path (P1), a continuous strip of impermeable material, which is intended to define a succession of sheets (3) of impermeable material; and
- at least one operating unit (8), which is arranged along the forming path (P1) and feeds a corresponding component of the hygiene absorbent articles (2) to the sheets (3) of impermeable material carried by the feeding line (7);

wherein the operating unit (8) comprises a processing device (9), which receives the components in succession and processes the components, and an application device (10), which receives the finished components from the processing device (9) and applies the components to the sheets (3) of impermeable material; and wherein the application device (10) comprises at least one sucking pick-up head (11) and a conveyor (12) to cyclically move the pick-up head (11) along an annular application path (P2), which extends through a pick-up station (S1), where the pick-up head (11) receives a corresponding component from the processing device (9), and a release station (S2), where the pick-up head (11) applies the component to a corresponding sheet (3) of impermeable material carried by the feeding line (7);

wherein the conveyor (12) comprises:
- an annular guide (14), which is arranged in a fixed position along the application path (P2);
- a slide (15), which supports the sucking pick-up head (11), is coupled to the guide (14) so as to freely slide along the guide (14), is "U"-shaped, embraces the guide (14) on both sides of the guide (14), and supports a plurality of wheels (23), which are fitted on the slide (15) in an idle manner and roll along respective rolling surfaces (24) of the guide (14); and
- a linear electric motor (16), which comprises a stator (17), which is arranged in a fixed position along the guide (14), and a mobile slider (18), which is electromagnetically coupled to the stator (17) so as to receive, from the stator (17), a driving force and is rigidly connected to the slide (15).

15. A maker machine (1) according to claim 14, wherein, on each side, the guide (14) comprises a pair of rolling surfaces (24), which are arranged at a given distance from one another, are oriented perpendicular to one another, and are coupled to corresponding wheels (23) of the slide (15).

* * * * *